United States Patent [19]

Snyder

[11] Patent Number: 4,580,053
[45] Date of Patent: Apr. 1, 1986

[54] BACKSCATTER DETECTION INSPECTION APPARATUS FOR TUBULAR GOODS

[75] Inventor: John E. Snyder, San Antonio, Tex.

[73] Assignee: William B. Wilson Mfg. Co., San Antonio, Tex.

[21] Appl. No.: 458,316

[22] Filed: Jan. 17, 1983

[51] Int. Cl.⁴ .................................... G01N 23/00
[52] U.S. Cl. ...................... 250/358.1; 250/359.1; 378/59
[58] Field of Search ............. 250/308, 358.1, 359.1, 250/360.1, 363 R; 378/59

[56] References Cited

U.S. PATENT DOCUMENTS

| 1,455,795 | 5/1923 | Logan . | |
|---|---|---|---|
| 2,665,387 | 1/1954 | Bartow . | |
| 2,932,744 | 4/1960 | Lehman . | |
| 3,046,430 | 7/1962 | Green . | |
| 3,069,549 | 12/1962 | Thompson . | |
| 3,107,276 | 10/1963 | Cohen . | |
| 3,275,831 | 9/1966 | Martin . | |
| 3,418,475 | 12/1968 | Hudgens . | |
| 3,569,708 | 3/1971 | Weinbaum et al. | 378/59 |
| 3,666,944 | 5/1972 | Baldinger . | |
| 3,683,187 | 8/1972 | Tompkins . | |
| 3,683,188 | 8/1972 | Hugonin . | |
| 3,684,887 | 8/1972 | Hugonin . | |
| 4,071,771 | 1/1978 | Covic et al. | 250/505 |
| 4,233,519 | 11/1980 | Coad . | |

Primary Examiner—Janice A. Howell
Attorney, Agent, or Firm—Cox & Smith Inc.

[57] ABSTRACT

Disclosed is a device employing radiation emission and backscatter detection for inspection of tubular goods for defects. A shutter mechanism is interposed between the radiation source and the tubular goods during inspection operations to control the transmission of radiation. The shutter mechanism is electrically activated to an open position and resiliently biased to a closed position. When the shutter mechanism is deactivated, it is automatically closed to prevent undesired emission of harmful radiation.

8 Claims, 4 Drawing Figures

BACKSCATTER DETECTION INSPECTION APPARATUS FOR TUBULAR GOODS

FIELD OF THE INVENTION

The present invention relates generally to apparatus for inspecting tubular goods for defects and more specifically to inspection apparatus utilizing radiation emission and backscatter detection.

BACKGROUND OF THE INVENTION

Tubular goods such as drill pipe and casing string sections are widely used in oil and gas exploration or production activities and like applications. Such tubular goods must be inspected for latent structural defects to prevent failure under working conditions. Radiation has been used for this purpose, with a detector situated either to sense radiation passing through a wall or to sense backscatter radiation from an irradiated surface.

Conventional backscatter detection inspection systems have incorporated a camera containing a radiation source. A camera in the context of this field of technology is an active emitter of energy, with the radiation detector considered as a separate, passive energy receptor. Radiation emission is directed toward the object to be inspected through an orifice in the camera regulated by an electrically activated, manually controlled shutter mechanism. These existing designs have recognized the risk of accidental exposure to radiation for operating personnel or others adjacent the device. This may occur if the shutter mechanism is left open, either by operator error or upon the loss of electrical power to the camera which enables the operator to manipulate the shutter mechanism. The risk of accidental exposure is drastically increased if a tubular member is not in position in front of the camera, such as may intermittently be the case during inspection operations. Under these conditions, radiation would be allowed to indiscriminately diffuse away from the camera without warning.

To counteract this, conventional designs have included a large block of radiation opaque material positioned across from the camera as a backup to absorb radiation which normally encounters a tubular member. However, this feature suffers from several undesirable inefficiencies and limitations. To the extent that radiation is still allowed to pass from the camera to the block with the shutter left open, a risk of accidental exposure remains. Secondly, the apparatus may become damaged to the point that the camera is misaligned and the block is rendered useless. Finally, backscatter detection inspection systems are frequently mounted on a flange which is rotated at high speed around an opening through which the tubular member is passed, in order to provide complete exposure to the radiation. This procedure is made considerably more difficult and less energy efficient by the presence of the massive block which must also be rapidly rotated with the camera during inspections.

Therefore, it is a feature of the invention to provide an improved backscatter detection inspection apparatus for tubular goods.

It is another feature of the invention to provide an improved radiation camera having a shutter mechanism which automatically prevents the emission of radiation upon the loss of electrical power to the camera.

These and other objects advantages and features of the invention will be apparent to those skilled in the art, from consideration of the specification, including the attached drawings and appended claims.

SUMMARY OF THE INVENTION

The present invention comprises a radiation camera and detector situated to irradiate and sense backscatter radiation from tubular goods, such as a pipe section. The camera includes a radiation opaque body having a chamber for containment of a radiation source. A collimating window terminates at one end at an orifice on the exterior of the camera body and communicates with the chamber to enable the transmission of radiation through the orifice towards the tubular goods.

The camera also includes a shutter mechanism for controlling the emission of radiation during inspection operations. The shutter mechanism comprises a radiation opaque gate slideably mounted on the camera body and biased by a spring to a closed position over the orifice, preventing radiation from leaving the camera. The gate is also connected to a solenoid which overcomes the spring when energized and shifts the gate to an open position enabling radiation to escape during inspection operations. When the solenoid is deenergizied, such as when electrical power to the camera is unintentionally lost, the gate is automatically shifted to the closed position to prevent accidental human exposure to radiation.

In one application, the invention includes a flange having a bracket supporting the camera and detector. The tubular member is passed through an opening in the flange while the flange is continuously rotated. The camera can assume one of three positions with respect to the bracket and flange. A scan position directs the radiation at the tubular goods during inspection operations. A load/unload position enables access to the radiation source through a door in the camera body. A closed position directs the orifice at a stationary radiation opaque shield when the apparatus is not in use.

BRIEF DESCRIPTION OF THE DRAWINGS

So that the manner in which the above-recited features, advantages and objectives of the invention, as well as others which will become apparent, are attained and can be understood in detail, a more particular description of the invention briefly summarized above may be had by reference to the embodiment thereof which is illustrated in the drawings, which drawings form a part of this specification. It is to be noted, however, that the appended drawings illustrate only a preferred embodiment of the invention and are therefore not to be considered limiting of its scope, for the invention may admit to other equally effective embodiments.

In the Drawings.

DETAILED DESCRIPTION OF THE INVENTION

Figure 1:
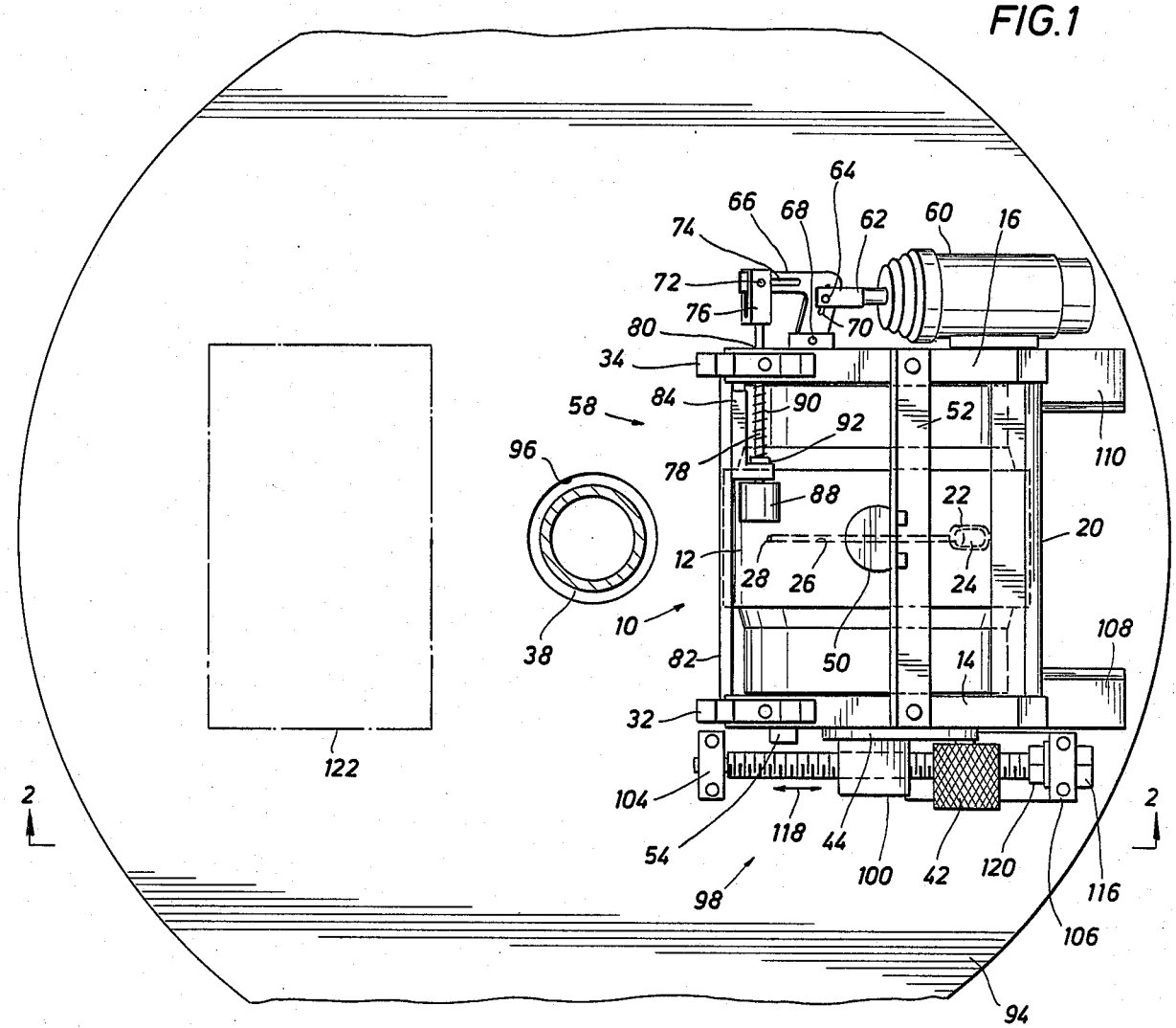
FIG. 1 is a top view of an inspection system according to the present invention.

Radiation camera 10 includes body 12 rotatably supported by guide plates 14 and 16 and parallel cross-flanges 18 and 20 and includes chamber 22, which chamber contains radiation source 24. In the preferred embodiment of the invention radiation source 24 emits gamma ray radiation, which has been found to be useful in applications to which the invention is directed. Body 12 is constructed of a radiation opaque material such as tungsten in at least those portions surrounding chamber 22 to protect adjacent operating personnel.

Collimating window 26 communicates with chamber 22 and enables radiation from source 24 to emerge from the body through orifice 28. Radiation detector 30 (not shown in FIGS. 1 and 3) is positioned by and clamped within aligned cradle portions 32 and 34 of the guide plates at critical angle of incidence 36 (shown in FIG. 2) with respect to the camera and pipe section 38 or the like. This arrangement maximizes the reception of backscatter radiation. In the preferred embodiment of the invention the radiation detector is a scintillation counter, which converts captured radiation impulses into electrical signals. Continuous monitoring of variations in the level of electrical signals while exposing various portions of the pipe section to radiation will pinpoint anomalies such as cracks, fractures or other latent defects as previously discussed.

Camera 10 is capable of assuming more than one position with respect to guide plates 14 and 16. To assist in shifting camera 10 between the alternative positions, either or both of the guide plates can include a slot such as arcuate groove 40 as in FIG. 2, which slidingly engages knurled knob 42. Knob 42 is connected through exterior radial arm 44 to body 12 of the camera to enable rotation and positioning of the camera at the desired orientation. During inspection operations the camera is in a scan position wherein orifice 28 is directed at pipe section 38 and knob 42 is as illustrated at 46. Secondly, the camera can assume a load/unload position, with knob 42 positioned at 46', enabling access to chamber 22 and radiation source 24 through door 48 provided in body 12. Thirdly, a closed position is available, with knob 42 positioned at 46", which directs orifice 28 at stationary shield 50 when the apparatus is not in use for extended periods of time. Shield 50 is positioned by cross flange 52 which is mounted at each end to guide plates 14 and 16. When directed at any of the positions 46, 46' and 46", lock 54 may be engaged with any of the corresponding notches 56, 56' and 56" so as to hold the camera in proper orientation and prevent unauthorized access or operation of the mechanism.

Shutter mechanism 58 is provided as part of camera 10 to control the emission of radiation when the camera assumes the scan position. The shutter mechanism includes solenoid 60 mounted on guide plate 16 and which is connected to first clevis 62 and first clevis pin 64. Bell crank arm 66 is pivotly connected to flange 68 on guide plate 16 and slidingly engages first clevis pin 64 in first slot 70 and also slideably engages second clevis pin 72 in second slot 74. Second clevis pin 72 is connected to second clevis 76 which in turn is connected to one end of rod 78. First slot 70 is obliquely oriented with respect to second slot 74 so as to enable the bell crank arm to convert radial movement of clevis 62 under the influence of solenoid 60 to longitudinally movement of the second clevis and rod parallel to the axis of the body 12.

An opening 80 is provided in guide plate 16 to slideably engage and support rod 78. In addition, cross flange 82 is mounted on the guide plates and supports rod stop block 84 which also slidingly engages and supports the rod. Cross flange 82 includes indentation 86 so as to avoid interference with orifice 28. The other end of rod 78 is connected to gate 88 which is slidingly mounted on body 12 and likewise constructed of a radiation opaque material such as tungsten. Spring 90 is provided in conjunction with annular flange 92 of rod 78 to bias the rod and gate to a closed position over orifice 28, thereby preventing the emission of radiation therefrom.

When electrically energized during inspection operations, solenoid 60 overcomes the spring force and shifts gate 88 to an open position, as shown uncovering orifice 28 which enables radiation to escape. When the solenoid is deenergized, the gate is automatically biased to the closed position by the spring. The solenoid can be deactivated intentionally, such as at the end of an inspection, or unintenionally, such as during the accidential loss of the electrical power to the apparatus. In either case, the shutter mechanism is automatically closed to prevent exposure of operating personnel to harmful doses of radiation. The need for operator intervention is obviated and the response time to an emergency situation is drastically reduced, the benefits of which may be readily appreciated.

Figure 2:
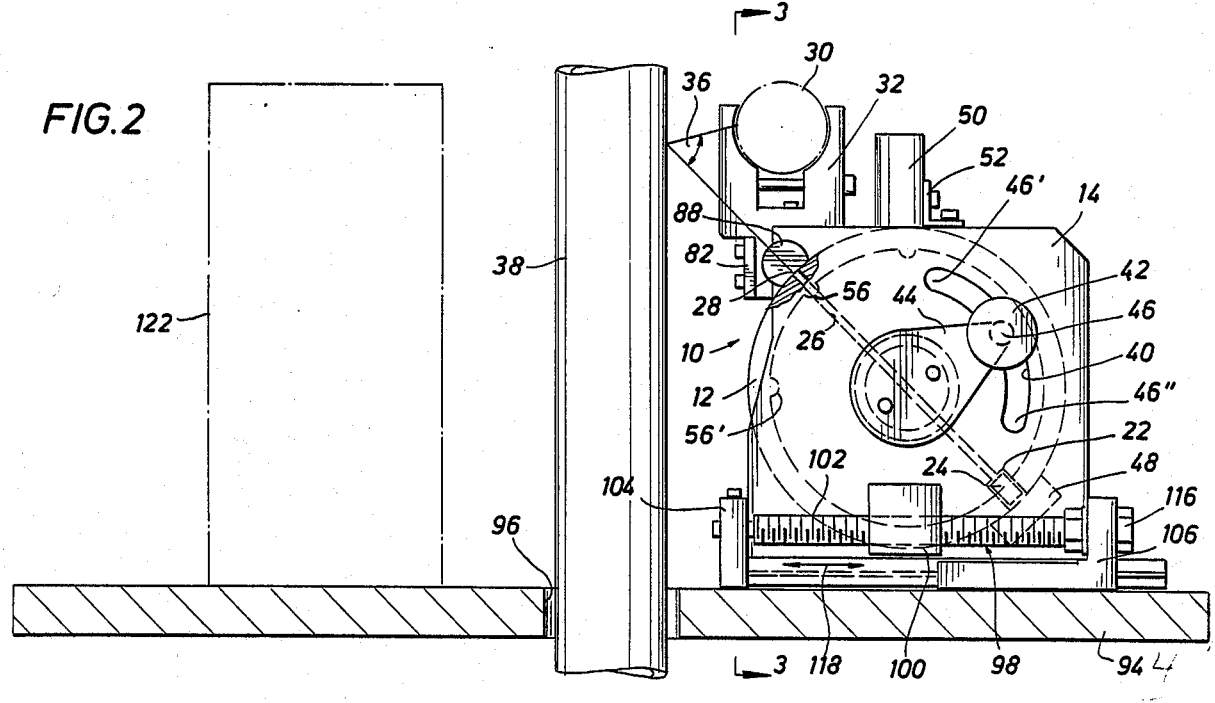
FIG. 2 is a side view along plane 2—2 of FIG. 1.

Referring now to FIGS. 1 and 2, in one embodiment of the invention, the inspection apparatus includes flange 94 having opening 96 in which pipe section 38 is positioned by a pipe handling mechanism (not shown). Adjustment mechanism 98 is provided to radially adjust the position of the camera and guide plates with respect to the pipe section and flange 94. The adjustment mechanism includes drive nut 100 mounted on guide plate 14, which drive nut threadedly engages drive gear 102. Drive gear 102 is rotatably supported at either end by bearing blocks 104 and 106 mounted on flange 94.

Figure 3:
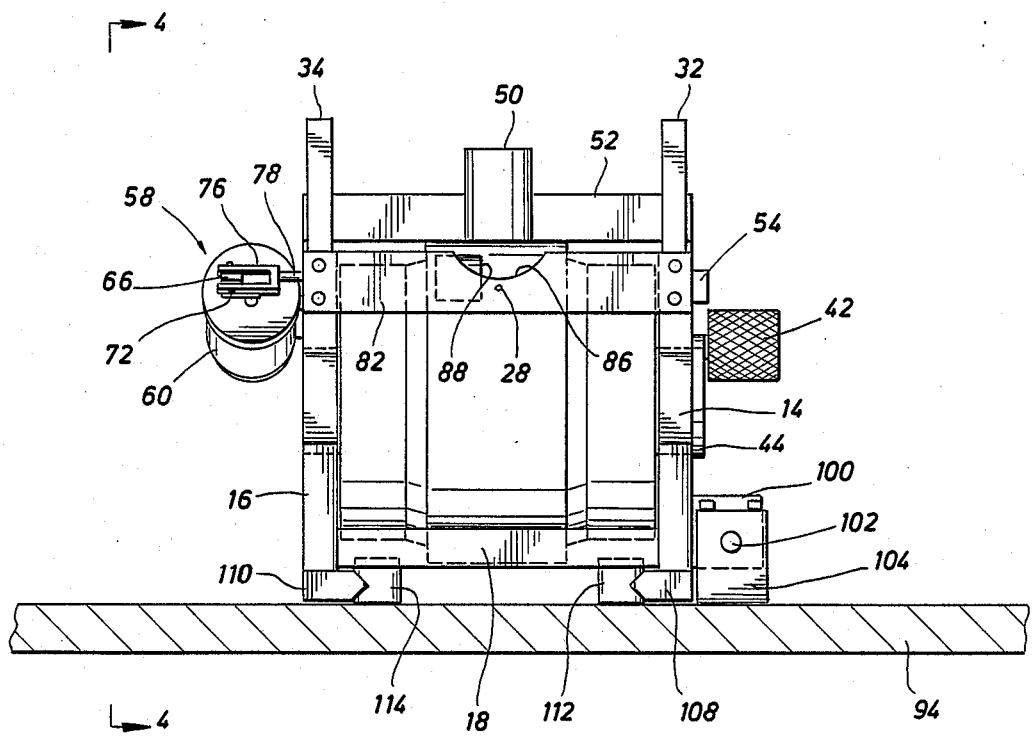
FIG. 3 is a sectional view along plane 3—3 of FIG. 1.
Figure 4:
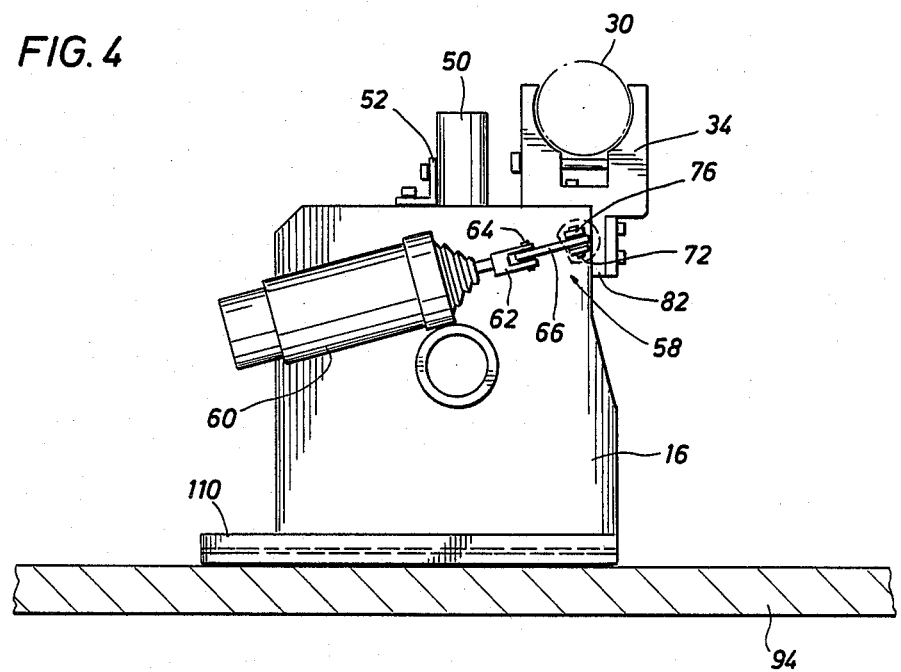
FIG. 4 is a side view along plane 4—4 of FIG. 1.

Guide plates 14 and 16 each include V-shaped male bearing portions 108 and 110 respectively, shown in FIG. 3. The bearing portions slideably engage V-shaped female bearing portions 112 and 114 which are mounted on flange 94. In the preferred embodiment of the invention, the V-shaped male bearing portions are constructed of brass, while the V-shaped female portions are constructed of stainless steel, so as to minimize friction and wear on the bearing surfaces. Relative rotation of the drive gear and drive nut induced through hex head 116 on the drive gear will enable movement of the camera along direction 118 of FIGS. 1 and 2, limited by jam nut 120 to obtain the critical angle of incidence as hereinabove described.

When it is desired to inspect pipe section 38, camera 10 assumes the scan position and the shutter mechanism is energized, assuming the open position. Relative rotation is established between flange 94 and the pipe section, while the pipe section is passed through opening 96 by the pipe handling mechanism to ensure complete exposure to the radiation and coverage by the detector. Relative rotation between the pipe section and the flange can be established by an electric motor (not shown) engaged with the flange or alternatively, by inducing rotation of the pipe section, such as by the pipe handling apparatus previously mentioned. Upon completion of the inspection process, the pipe section 38 is removed from opening 96 and replaced with a like object for further operation.

Conventional rotating backscatter detection inspection systems would have required the addition of a massive block of radiation absorbing material as at 122, which is completely obviated by the automatic functioning of the shutter mechanism of the present invention.

From the foregoing, it will be seen that this invention is one well adapted to attain all of the ends and objects hereinabove set forth, together with other advantages that are obvious and that are inherent to the apparatus and structure. It will be understood that certain features and subcombinations are of utility and may be employed without reference to other features and subcombinations. This is contemplated by and is within the scope of the claims.

Because many possible embodiments may be made thereof, it is to be understood that all matters herein set forth, and shown in the accompanying drawings, are to be interpreted as illustrative and not in a limiting sense, and equivalent structures will become apparent to those skilled in the art to which the invention pertains.

What is claimed is:

1. An apparatus employing radiation emission and backscatter detection for inspection of tubular goods for defects, comprising:
   a camera, including:
     a radiation source,
     a housing constructed at least partially of radiation opaque material having a chamber for containing said radiation source and a window communicating with said chamber for directing radiation exteriorly of said housing toward the tubular goods,
     a shutter mechanism mounted with said housing for controlling the emission of radiation therefrom, being electrically activated to an open position for enabling the transmission of radiation and being resiliently biased to a closed position when deactivated so as to automatically prevent the emission of radiation;
   a radiation detector mounted with said camera for sensing backscatter radiation from the tubular goods;
   a flange for positioning said camera and detector with respect to the tubular goods, having an opening for passage of the tubular goods, and including a bracket for supporting said camera and said radiation detector;
   pipe handling means for passing the tubular goods through said opening; and
   spinning means for establishing relative rotation between said flange and the tubular goods so as to expose all portions of the tubular goods to radiation.

2. The apparatus as set forth in claim 1, wherein said shutter mechanism comprises:
   a gate constructed of radiation opaque material slidably mounted on said housing and shiftable between a first position over said window and a second position uncovering said window;
   a solenoid mounted with said camera and connected to said gate for shifting said gate to said second position when electrically activated; and
   a spring mounted on said housing in contact with said gate for urging said gate to said first position, whereby transmission of radiation from said housing is automatically prevented when said solenoid is deactivated.

3. The apparatus as set forth in claim 1, further comprising:
   a door mounted on said housing for enabling access to said radiation source, said housing being shiftable with respect to said bracket from a position wherein said window is directed towards the tubular goods to a position wherein said door is exteriorly accessible.

4. The apparatus as set forth in claim 3 further comprising:
   a shield constructed of a radiation opaque material mounted on said bracket, said housing being further shiftable to a third position wherein said window is directed towards said shield.

5. The apparatus as set forth in claim 1, further comprising:
   adjustment means for shifting the location of said camera on said flange with respect to the longitudinal axis of the tubular goods.

6. The apparatus as set forth in claim 1, wherein: said radiation source emits gamma ray radiation.

7. The apparatus as set forth in claim 1, wherein: said radiation detector is a scintillation counter.

8. The apparatus as set forth in claim 1, wherein: the tubular goods are drill and casing string members.

* * * * *